United States Patent [19]

Escobedo et al.

[11] Patent Number: 6,110,737
[45] Date of Patent: Aug. 29, 2000

[54] HUMAN PLATELET-DERIVED GROWTH FACTOR RECEPTOR, TYPE A

[75] Inventors: Jaime A. Escobedo; Lewis T. Williams, both of San Francisco, Calif.

[73] Assignee: The Regents of the University of California, Berkeley, Calif.

[21] Appl. No.: 08/240,294

[22] Filed: May 9, 1994

Related U.S. Application Data

[63] Continuation of application No. 08/031,082, Mar. 15, 1993, abandoned, which is a continuation of application No. 07/771,829, Oct. 7, 1991, abandoned, which is a continuation of application No. 07/309,322, Feb. 10, 1989, abandoned, which is a continuation-in-part of application No. 07/151,414, Feb. 2, 1988, abandoned.

[51] Int. Cl.$^7$ .............................. C12N 1/19; C12N 5/16; C12N 15/81; C12N 15/85

[52] U.S. Cl. .................. 435/325; 435/254.2; 435/320.1; 435/358; 435/361; 435/455; 435/471; 536/23.1; 536/23.5; 536/24.31

[58] Field of Search .............................. 435/172.3, 240.2, 435/320.1, 455, 471, 325, 254.2, 358, 361; 536/23.1, 23.5, 24.31; 935/27, 34, 70

[56] References Cited

U.S. PATENT DOCUMENTS 5,371,205  12/1994  Kelly et al. ............................ 536/23.5

FOREIGN PATENT DOCUMENTS

| 0 325 224 | 7/1989 | European Pat. Off. ........ C12N 15/00 |
| 0 327 369 | 8/1989 | European Pat. Off. ........ C12N 15/00 |
| WO 90/10013 | 9/1990 | WIPO ............................. C07H 21/04 |

OTHER PUBLICATIONS

Escobedo et al. (1988) "A Common PDGF Receptor Is Activated by Homodimeric A and B Forms of PDGF" *Science* 240:1532–1534.

Kazlauskas et al. (1988) "Different effects of homo– and heterodimers of platelet–derived growth factor A and B chains on human and mouse fibroblasts" *EMBO J.* 7:3727–3735.

Hart et al. (1988) "Two Classes of PDGF Receptor Recognize Different Isoforms of PDGF" *Science* 240:1529–1531.

Escobedo et al. (1988) "Platelet–derived Growth Factor Receptors Expressed by cDNA Transfection Couple to a Diverse Group of Cellular Responses Associated with Cell Proliferation" *J. Biol. Chem.* 263:1482–1487.

Yarden et al. (1986) "Structure of the receptor for platelet-–derived growth factor helps define a family of closely related growth factor receptors" *Nature* 323:226–232.

Gronwald et al. (1988) "Cloning and expression of a cDNA coding for the human platelet–derived growth factor receptor: Evidence for more than one receptor class" *Proc. Nat'l Acad. Sci. USA* 85:3435–3439.

Glenn et al. (1982) "Platelet–derived Growth Factor" *J. Biol. Chem.* 257:5172–5176.

Haynes et al. (1983) "Constitutive, long–term production of human interferons by hamster cells containing multiple copies of a cloned interferon gene" *Nucl. Acids Res.* 11:687–706.

Peralta et al. (1987) "Primary Structure and Biochemical Properties of an $M_2$ Muscarinic Receptor" *Science* 236:600–605.

Heldin et al. (1982) "Interaction of Platelet–derived Growth Factor with Its Fibroblast Receptor" *J. Biol. Chem.* 257:4216–4221.

Daniel et al. (1985) "Purification of the platelet–derived growth factor receptor by using an anti–phosphotyrosine antibody" *Proc. Nat'l Acad. Sci. USA* 82:2684–2687.

Claesson–Welsh et al. (1988) "cDNA Cloning and Expression of a Human Platelt–Derived Growth Factor (PDGF) Receptor Specific for B–Chain–Containing PDGF Molecules" *Mol. Cell. Biol.* 8:3476–3486.

Williams (1989) "Signal Transduction by the Platelet–Derived Growth Factor Receptor" *Science* 243:1564–1570.

Williams et al. (1986) "PDGF receptors: Structural and Functional Studies" *Miami Winter Symposium* 1986, ICSU Press.

Williams et al. (1988) "The Immunoglobulin Superfamily–Domains for Cell Surface Recognition" *Ann. Rev. Immunology* 6:381–405.

Williams (1988) "Stimulation of Paracrine and Autocrine Pathways of Cell Proliferation by Platelet–Derived Growth Factor" *Clinical Research* 36:5–10.

Williams et al. (1987) "The Stimulation of Paracrine and Autocrine Mitogenic Pathways by the Platelet–Derived Growth Factor Receptor" *J. Cell Physiol. Supp.* 5:27–30.

Fantl et al. (1989) "Mutations of the Platelet–Derived Growth Factor Receptor That Cause a Loss of Ligand–Induced Conformational Change, Subtle Changes in Kinase Activity, and Impaired Ability To Stimulate DNA Synthesis" *Mol. Cell. Biol.* 9:4473–4478.

Yarden et al. (1988) "Growth Factor Receptor Tyrosine Kinases" *Ann. Rev. Biochem.* 57:443–78.

Ullrich et al. (1990) "Signal Transduction by Receptors with Tyrosine Kinase Activity" *Cell* 61:203–212.

(List continued on next page.)

*Primary Examiner*—Scott D. Priebe
*Attorney, Agent, or Firm*—Burns, Doane, Swecker & Mathis, L.L.P.

[57] ABSTRACT

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

10 Claims, 10 Drawing Sheets

OTHER PUBLICATIONS

Claesson–Welsh et al. (1989) "cDNA cloning and expression of the human A–type platelet–derived growth factor (PDGF) receptor establishes structural similarity to the B–type PDGF receptor" *Proc. Nat'l Acad. Sci. USA* 86:4917–4921.

Matsui et al. (1989) "Isolation of a Novel Receptor cDNA Establishes the Existence of Two PDGF Receptor Genes" *Science* 243:800–803.

Ruta et al. (1988) "A novel protein tyrosine kinase gene whose expression is modulated during endothelial cell differentiation" *Oncogene* 3:9–15.

Reid et al. (1990) "Two forms of the basic fibroblast growth factor receptor–like mRNA are expressed in the developing mouse brain" *Proc. Nat'l Acad. Sci. USA* 87:1596–1600.

Kornbluth et al. (1988) "Novel Tyrosine Kinase Identified by Phosphotyrosine Antibody Screening of cDNA Libraries" *Mol. Cell. Biol.* 8:5541–5544.

Escobedo et al. (1988) "Role of Tyrosine Kinase and Membrane–Spanning Domains in Signal Transduction by the Platelet–Derived Growth Factor Receptor" *Mol. Cell. Biol.* 8:5126–5131.

Qiu et al. (1988) "Primary structure of c–kit: relationship with the CSF–1/PDGF receptor kinase family–oncogenic activation of v–kit involves deletion of extracellular domain and C terminus" *EMBO J.* 7:1003–1011.

Hart et al. (1989) "Expression of Secreted Human Immunoglobulin/PDGF–Receptor Fusion Proteins Which Demonstrate High Affinity Ligand Binding" *Miami Winter Cancer Symposium*, abstract.

Heldin et al. (1988) "Binding of different dimeric forms of PDGF to human fibroblasts: evidence for two separate receptor types" *EMBO J.* 7:1387–1393.

Daniel et al. (1987) "Biosynthetic and Glycosylation Studies of Cell Surface Platelet–derived Growth Factor Receptors" *J. Biol. Chem.* 262:9778–9784.

Keating et al. (1989) "Platelet–derived Growth Factor Receptor Inducibility Is Acquired Immediately after Translation and Does Not Require Glycosylation" *J. Biol. Chem.* 264:9129–9132.

Keating et al. (1988) "Autocrine Stimulation of Intracellular PDGF Receptors in v–sis–Transformed Cells" *Science* 239:914–916.

Hart et al. (1987) "Synthesis, Phosphorylation, and Degradation of Multiple Forms of the Platelet–derived Growth Factor Receptor Studied Using a Monoclonal Antibody" *J. Biol. Chem.* 262:10780–10785.

Bell et al. (1989) "Effect of Platelet Factors on Migration of Cultured bovine Aortic Endothelial and Smooth Muscle Cells" *Circulation Research* 65:1057–1065.

Ronnstrand et al. (1987) "Purification of the Receptor for Platelet–derived Growth Factor from Porcine Uterus" *J. Biol. Chem.* 262:2929–2932.

Felder et al. (1990) "Kinase Activity Controls the Sorting of the Epidermal Growth Factor Receptor within the Multivesicular Body" *Cell* 61:623–634.

Orchansky et al. (1988) "Phosphatidylinositol Linkage of a Truncated Form of the Platelet–derived Growth Factor Receptor" *J. Biol. Chem.* 263:15159–15165.

Kimball et al. (1984) "Epidermal Growth Factor (EGF) Binding to Membranes Immobilized in Microtiter Wells and Estimation of EGF–Related Transforming Growth Factor Activity" *Biochim. Biophys. Acta* 771:82–88.

van der Schaal et al. (1984) "An Enzyme–Linked Lectin Binding Assay for Quantitative Determination of Lectin Receptors" *Anal. Biochem.* 140:48–55.

van Driel et al. (1989) "Stoichiometric Binding of Low Density Lipoprotein (LDL) and Monoclonal Antibodies to LDL Receptors in a Solid Phase Assay" *J. Biol. Chem.* 264:2533–9538.

Williams et al. (1982) "Platelet–derived growth factor binds specifically to receptors on vascular smooth muscle cells and the binding becomes nondissociable" *Proc. Nat'l Acad. Sci. USA* 79:5867–5870.

Williams et al. (1984) "Platelet–derived Growth Factor Receptors Form a High Affinity State in Membrane Preparations" *J. Biol. Chem.* 259:5287–5294.

Anderson et al. (1990) "Binding of SH2 Domains of Phospholipase $C_\gamma 1$, GAP, and Src to Activated Growth Factor Receptors" *Science* 250:979–982.

Coughlin et al. (1989) "Role of Phosphatidylinositol Kinase in PDGF Receptor Signal Transduction" *Science* 243:1191–1194.

Escobedo et al. (1988) "A PDGF receptor domain essential for mitogenesis but not for many other responses to PDGF" *Nature* 335:85–87.

Williams et al. (1988) "Signal Transduction by the Platelet–derived Growth Factor Receptor" *CSH Symp. Quant. Biol.* 53:455–465.

Morrison et al. (1989) "Direct Activation of the Serine/Threonine Kinase Activity of Raf–1 through Tyrosine Phosphorylation by the PDGF β–Receptor" *Cell* 58:649–657.

Keating et al. (1988) "Ligand Activation Causes a Phosphorylation–dependent Change in Platelet–derived Growth Factor Receptor Conformation" *J. Biol. Chem.* 263:12805–12808.

Morrison et al. (1990) "Platelet–Derived Growth Factor (PDGF)–Dependent Association of Phospholipase c–τ with the PDGF Receptor Signaling Complex" *Mol. Cell. Biol.* 10:2359–2366.

Kaplan et al. (1990) "PDGF β–Receptor Stimulates Tyrosine Phosphorylation of GAP and Association of GAP with a Signaling Complex" *Cell* 61:125–133.

Roussel et al. (1987) "Transforming Potential of the c–fms Proto–oncogene (CSF–1 Receptor)" *Nature* 325:549–552.

Moran et al. (1990) "Src Homology Region 2 Domains Direct Protein–Protein Interactions in Signal Transduction" *Proc. Nat'l Acad. Sci. USA* 87:8622–8626.

Kypta et al. (1990) "Association Between the PDGF Receptor and Members of the src Family of Tyrosine Kinases" *Cell* 62:401–492.

Heidaran et al. (1990) "Chimeric α– and β–Platelet–derived Growth Factor (PDGF) Receptors Define Three Immunoglobulin–like Domains of the α–PDGF Receptor That Determine PDGF–AA Binding Specificity" *J. Biol. Chem.* 265:18741–18744.

Marx (1990) "Oncogenes Evoke New Cancer Therapies" *Science* 249:1376–1378.

Keating et al. (1987) "Processing of the Platelet–derived Growth Factor Receptor" *J. Biol. Chem.* 262:7932–7937.

Bishayee et al. (1989) "Ligand–induced dimerization of the Platelet–derived Growth Factor Receptor" *J. Biol. Chem.* 264:11699–11705.

Seifert et al. (1989) "Two Different Subunits Associate to Create Isoform–specific Platelet–derived Growth Factor Receptors" *J. Biol. Chem.* 264:8771–8778.

Nister et al. (1988) "A Glioma–Derived PDGF A Chain Homodimer Has Different Functional Activities from a PDGF AB Heterodimer Purified from Human Platelets" *Cell* 52:791–799.

Williams (1989) "Signal Transduction by the Platelet–Derived Growth Factor Receptor Involves Association of the Receptor with Cytoplasmic Molecules" *Clinical Research* 37:564–568.

Heldin et al. (1989) "Dimerization of B–type Platelet–derived Growth Factor Receptors Occurs after Ligand Binding and Is Closely Associated with Receptor Kinase Activation" *J. Biol. Chem.* 264:8905–8912.

C. Betsholtz et al. (1984) "Coexpression of a PDGF–like Growth Factor and PDGF Receptors in Human Osteosarcoma Cell Line: Implications for Autocrine Receptor Activation", *Cell* 39:447–457.

N. Giese et al. (1987) "The Role of Individual Cysteine Residues in the Structure and Function of the v–sis Gene Product" *Science* 236:1315–1318.

FIGURE 1A

```
Asn Phe Glu Trp Thr Tyr Pro Arg Lys Glu Ser Gly Arg Leu Val Glu Pro Val Thr Asp Phe Leu Leu Asp Met Pro Tyr His Ile Arg
AAC TTC GAG TGG ACA TAC CCC CGC AAA GAA AGT GGG CGG CTG GTG GAG CCG GTG ACT GAC TTC CTC TTG GAT ATG CCT TAC CAC ATC CGC
                          220                           230                           240

Ser Ile Leu His Ile Pro Ser Ala Glu Leu Glu Asp Ser Gly Thr Tyr Thr Cys Asn Val Thr Glu Ser Val Asn Asp His Gln Asp Glu
TCC ATC CTG CAC ATC CCC AGT GCC GAG TTA GAA GAC TCG GGG ACC TAC ACC TGC AAT GTG ACG GAG AGT GTG AAT GAC CAT CAG GAT GAA
          250                           260                           270

Lys Ala Ile Asn Ile Thr Val Val Glu Ser Gly Tyr Val Arg Leu Leu Gly Thr Leu Gln Phe Ala Glu Leu His Arg Ser
AAG GCC ATC AAC ATC ACC GTG GTT GAG AGC GGC TAC GTG CGG CTC CTG GGA ACA CTA CAA TTT GCT GAG CTG CAT CGG AGC
                  280                           290                           300

Arg Thr Leu Gln Val Val Phe Glu Ala Tyr Pro Pro Thr Val Leu Trp Phe Lys Asp Asn Arg Thr Leu Gly Asp Ser Ser Ala Gly
CGG ACA CTG CAG GTA GTG TTC GAG GCC TAC CCA CCG ACT GTC CTG TGG TTC AAA GAC AAC CGC ACC CTG GGC GAC TCC AGC GCT GGC
          310                           320                           330

Glu Ile Ala Leu Ser Thr Arg Asn Val Ser Glu Thr Leu Thr Val Lys Val Ala Glu Ala Arg His
GAA ATC GCC CTG TCC ACG CGC AAC GTG TCG GAG ACC CTG ACA GTG AAG GTG GCA GAG GCT CGC CAC
                  340                           350                           360

Tyr Thr Met Arg Ala Phe His Glu Asp Ala Glu Val Gln Leu Ser Phe Gln Leu Gln Ile Asn Val Pro Val Arg Val Leu Glu Leu Ser
TAC ACC ATG CGG GCC TTC CAT GAG GAT GCT GAG GTC CAG CTC TCC TTC CAG CTA CAG ATC AAT GTC CCT GTC CGA GTG CTG GAG CTA AGT
          370                           380                           390

Glu Ser His Pro Asp Ser Gly Glu Gln Thr Val Arg Cys Arg Gly Met Pro Gln Pro Asn Ile Ile Trp Ser Ala Cys Arg Asp
GAG AGC CAC CCT GAC AGT GGG GAA CAG ACA GTC CGG TGT CGT GGC ATG CCC CAG CCG AAC ATC ATC TGG TCT GCC TGC AGA GAC
                  400                           410                           420

Leu Lys Arg Cys Pro Arg Glu Leu Pro Pro Thr Leu Leu Gly Asn Ser Ser Glu Glu Glu Thr Gln Leu Glu Thr Asn Val Thr Tyr Trp
CTC AAA AGG TGT CCA CGT GAG CTG CCG CCC ACG CTG CTG GGG AAC AGT TCC GAA GAG GAG ACC CAG CTG GAG ACT AAC GTG ACG TAC TGG
          430                           440                           450

Glu Glu Gln Gln Glu Phe Glu Val Val Ser Thr Leu Arg Leu Gln His Val Asp Arg Pro Leu Ser Val Arg Cys Thr Leu Arg Asn Ala
GAG GAG CAG CAG GAG TTT GAG GTG GTG AGC ACA CTG CGT CTG CAG CAC GTG GAT CGG CCA CTG TCG GTG CGC TGC ACG CTG CGC AAC GCT
                  460                           470                           480

Val Gly Gln Asp Thr Gln Glu Val Ile Val Val Pro His Ser Leu Pro Phe Lys Val Val Val Ile Ser Ala Ile Leu Ala Leu Val Val
GTG GGC CAG GAC ACG CAG GAG GTC ATC GTG GTG CCA CAC TCC TTG CCC TTT AAG GTG GTG GTG ATC TCA GCC ATC CTG GCC CTG GTG GTG
          490                           500                           510
```

FIGURE 1B

```
Leu Thr Ile Ile Ser Leu Ile Ile Met Leu Trp Gln Lys Pro Arg Tyr Glu Ile Arg Trp Lys Val Ile Glu Ser Val Ser
CTC ACC ATC ATC TCC CTT ATC ATC ATG CTT TGG CAG AAG CCA CGT TAC GAG ATC CGA TGG AAG GTG ATT GAG TCT GTG AGC
                        520                           530                           540

Ser Asp Gly His Glu Tyr Ile Tyr Val Asp Pro Met Gln Leu Pro Tyr Asp Ser Thr Trp Glu Leu Pro Arg Asp Gln Leu Val Leu Gly
TCT GAC GGC CAT GAG TAC ATC TAC GTG GAC CCC ATG CAG CTG CCC TAT GAC TCC ACG TGG GAG CTG CCG CGG GAC CTT GTG CTG GGA
              550                           560                           570

Arg Thr Leu Gly Ser Gly Ala Phe Gly Gln Val Val Glu Ala His Gly Leu Ser His Ser Gln Ala Thr Met Lys Val Ala Val
CGC ACC CTC GGC TCT GGG GCC TTT GGG CAG GTG GTG GAG GCT CAT GGC CTG AGC CAT TCT CAG GCC ACG ATG AAA GTG GCC GTC
              580                           590                           600

Lys Met Leu Lys Ser Thr Ala Arg Ser Ser Glu Lys Gln Ala Leu Met Ser Glu Leu Lys Ile Met Ser His Leu Gly Pro His Leu Asn
AAG ATG CTT AAA TCC ACA GCC CGC AGC AGT GAG AAG CAA GCC CTT ATG TCG GAG CTG AAG ATC ATG AGT CAC CTT GGG CCC CAC CTG AAC
              610                           620                           630

Val Val Asn Leu Leu Gly Ala Cys Thr Lys Gly Gly Pro Ile Tyr Ile Ile Thr Glu Tyr Cys Arg Tyr Gly Asp Leu Val Asp Tyr Leu
GTG GTC AAC CTG TTG GGG GCC TGC ACC AAG GGA GGA CCC ATC TAT ATC ATC ACT GAG TAC TGC CGC TAC GGA GAC CTG GTG GAC TAC CTG
              640                           650                           660

His Arg Asn Lys His Thr Phe Leu Gln His His Ser Asp Lys Arg Arg Pro Pro Ser Ala Glu Leu Tyr Ser Asn Ala Leu Pro Val Gly
CAC CGC AAC AAA CAC ACC TTC CTG CAG CAC CAC TCC GAC AAG CGC CGC CCG CCC AGC GCG GAG CTC TAC AGC AAT GCT CTG CCC GTT GGG
              670                           680                           690

Val Pro Leu Pro Ser His Val Ser Leu Thr Gly Glu Ser Asp Gly Gly Tyr Met Asp Met Ser Lys Asp Glu Ser Val Asp Tyr Val Pro
GTC CCC CTG CCC AGC CAT GTG TCC TTG ACC GGG GAG AGC GAC GGT GGC TAC ATG GAC ATG AGC AAG GAC GAG TCG GTG GAC TAT GTG CCC
              700                           710                           720

Met Leu Asp Met Lys Gly Asp Val Lys Tyr Ala Asp Ile Glu Ser Ser Asn Tyr Met Ala Pro Tyr Asp Asn Tyr Val Pro Ser Ala Pro
ATG CTG GAC ATG AAA GGA GAC GTC AAA TAT GCA GAC ATC GAG TCC TCC AAC TAC ATG GCG CCT TAC GAT AAC TAC GTT CCC TCC GCC CCT
              730                           740                           750

Glu Arg Thr Cys Arg Ala Thr Leu Ile Asn Glu Ser Pro Val Leu Ser Tyr Met Asp Leu Val Gly Phe Ser Tyr Gln Val Ala Asn Gly
GAG AGG ACC TGC CGA GCA ACT TTG ATC AAC GAG TCT CCA GTG CTA AGC TAC ATG GAC CTC GTG GGC TTC AGC TAC CAG GTG GCC AAT GGC
              760                           770                           780
```

```
                                                                              790                                    800                                            810
Met Glu Phe Leu Ala Ser Lys Asn Cys Val His Arg Asp Leu Ala Ala Arg Asn Val Leu Val Lys Ile Cys
ATG GAG TTT CTG GCC TCC AAG AAC TGC GTC CAC AGA GAC CTG GCG GCT AGG AAC GTG CTC GTC AAG ATC TGT 820                                              830                                           840
Asp Phe Gly Leu Ala Arg Asp Ile Met Arg Ala Ser Asn Tyr Ile Ser Lys Gly Ser Thr Phe Leu Pro Leu Lys Trp Met Ala Pro Glu
GAC TTT GGC CTG GCT CGA GAC ATC ATG CGG GCC TCG AAT TAC ATC TCC AAA GGC AGC ACC TTT TTG CCT TTA AAG TGG ATG GCT CCG GAG 850                                            860                                           870
Ser Ile Phe Asn Ser Leu Tyr Thr Thr Leu Ser Asp Val Trp Ser Phe Gly Ile Leu Leu Trp Glu Ile Phe Thr Leu Gly Gly Thr Pro
AGC ATC TTC AAC AGC CTC TAC ACC ACC CTG AGC GAC GTG TGG TCC TTC GGG ATC CTG CTC TGG GAG ATC TTC ACC TTG GGT GGC ACC CCT 880                                              890                                              900
Tyr Pro Glu Leu Pro Met Asn Glu Gln Phe Tyr Asn Ala Ile Lys Arg Gly Tyr Arg Met Ala Gln Pro Ala His Ala Ser Asp Glu Ile
TAC CCA GAG CTG CCC ATG AAC GAG CAG TTC TAC AAT GCC ATC AAA CGG GGT TAC CGC ATG GCC CAG CCT GCC CAT GCC TCC GAC GAG ATC 910                                            920                                            930
Tyr Glu Ile Met Gln Lys Cys Trp Glu Glu Lys Phe Glu Ile Arg Pro Pro Phe Ser Gln Leu Val Leu Leu Leu Glu Arg Leu Leu Gly
TAT GAG ATC ATG CAG AAG TGC TGG GAA GAG AAG TTT GAG ATT CGG CCC CCC TTC TCC CAG CTG GTG CTT CTC GAG AGA CTG TTG GGC 940                                              950                                             960
Glu Gly Tyr Lys Lys Lys Tyr Gln Gln Val Asp Glu Glu Phe Leu Arg Ser Asp His Pro Ala Ile Leu Arg Ser Gln Ala Arg Leu Pro
GAA GGT TAC AAA AAG AAG TAC CAG CAG GTG GAT GAG GAG TTT CTG CGG AGT GAC CAC CCA GCC ATC CTT CGG TCC CAG GCC CGC TTG CCT 970                                           980                                              990
Gly Phe His Gly Leu Arg Ser Pro Leu Asp Thr Ser Ser Val Leu Tyr Thr Ala Val Gln Pro Asn Glu Gly Asp Asn Asp Tyr Ile Ile
GGG TTC CAT GGC CTC CGA TCT CCC CTG GAC ACC AGC AGC GTC CTC TAT ACT GCC GTG CAG CCC AAT GAG GGT GAC AAC GAC TAT ATC ATC 1000                                             1010                                             1020
Pro Leu Pro Asp Pro Lys Pro Glu Val Ala Asp Glu Gly Pro Leu Glu Gly Ser Pro Ser Leu Ala Ser Ser Thr Leu Asn Glu Val Asn
CCC CTG CCT GAC CCC AAA CCC GAG GTT GCT GAC GAG GGC CCA CTG GAG GGT TCC CCC AGC CTA GCC AGC AGC ACC CTG AAT GAA GTC AAC 1030                                           1040                                             1050
Thr Ser Thr Ile Ser Cys Asp Ser Pro Leu Glu Pro Gln Asp Glu Pro Glu Pro Glu Pro Gln Leu Glu Leu Gln Val Glu Pro Glu
ACC TCC ACC ATC TCC TGT GAC AGC CCC CTG GAG CCC CAG GAC GAA CCA GAG CCC GAG CCC CAG CTT GAG CTC CAG GTG GAG CCG GAG
```

1060                                   1070                                     1074
Pro Glu Leu Gln Leu Pro Asp Ser Gly Cys Pro Ala Pro Arg Ala Glu Ala Glu Asp Ser Phe Leu AM
CCA GAG CTG CAG CAG TTG CCG GAT TCG GGG TGC CCT GCG CCT CGG GCT GAA GCA GAG GAT AGC TTC CTG TAG GGGGCTGGCCCCTACCCTGCCCTG

CCTGAAGCTCCCCCCCTGCCAGCACCCAGCATCTCTGGCTGCCTGGCCGGGCTTCCTGTCCCCTTCTGGAAGCTTTCTGCTCCTGACGTGTT
GTGCCCCAAACCCTGGGGCTTGGCTTAGGAGGCAAGAAAACTGCAGGGCCCGTGACCAGCCCTCTGCCTCTGACTCTGACTCTCAGGAGGCCAACTGACTCTCAGGGTTCCCCAGGAACTCAGTTTT
CCCATATGTAAAATGGAAAGTTAGGCTTGATGACCAGAATCTAGAATTCTCTCCCTCGAATTCCTCCCTGGCTGACAGGTGGGAGACCAGGAGCTAGGAGACCCTAGCCTCTGGGATCTTGGAGTTACTGAGGTGGTA
AATTAACTTTTTTCTGTTCAGCCAGCTACCCCTCAAGGAATCATAGCTCTCTCCCTATGATGGCCAGTAGCACACCATAGAGCACACCATCTGTGGAAGACCACAGTCGTTTCCTGGCCTGTCGGGGACTAATGGAGCAGCCTAATTAATGCTGG
CCTAGCCTTGAGCAGTGTTGCCTCATCCAGAAGAGCCAGTTCTCCATCATGGCCAGTAGCACACCATAGAGCACACCATCTGTGGACAAGTCCTGTCCCTGTCCTTCAGGCCCATCAGTCCTGGGGCTTTTT
AGGCTGAGCCAAGTACAGGACACCCCAGCCTGCAGCCTTGAGACAACGGGCCCCGACATCTGATGAGAATGTAAATGCCAGTGTGGAGTGGCCACGTGTGTGTGCCAGTATATG
CTTTATCACCCTCAGTCTTAATCATCCACCAGAGTCTTAGAAGGCCAGACGGGCCCCGACATCTGATGAGAATGTAAATGCCAGTGTGGAGTGGCCACGTGTGTGTGCCAGTATATG
GCCCTGGCTCTGCATTGAGAGTATTCAGGTGGTTGCACATTTGTCCAGATGAAGCAAGCCATATACCCTAAACTTCCATCCTGGGGTCAGCTGGGCTCCTGGAGATTCCAGATCACACATC
CACTAACATTCTGGGGACTCAGGAACCATGCCCCTTCCCAGGCCCAGCAAGTCTCAAGAACACAGCTGACTTAGAGTGACAGCCGGTGTCCTGAAAGCCACCACTCCAG
CCCCAGGACATGGCCGAGGTCTGCGTCGAGAACAGAATGGACACAGTGAGGCAGTTGGTTTTGTCACTGCCCCAGACAACAAGAGCCTCAGTGACATCTCATTGTCCCAGCCAGTGGGCGCTTTGGA
GGTTTGCCCCTCACCACAGCGGGAGCTGTCCAAGAGTGTAGCCAAGAGGGGAGTGGGTTCTCAATACGTACCAAAGATATAATCACCTAGGTTACAAGATATAATCACCTAGGTTACAAAGAAGCTCAACCCCTGCATTGCAGTTCAGTTGGCACTTACTTCCCT
GGGATCCCAGGAGTTGGTCCAAGGAGGGAGTGGGTTCTCAATACGTACCAAAGATATAATCACCTAGGTTAACTCACATTTATACAGCAGAA
ATGCTATTTTTGTGATGCGTTAAGTTTTTCTATCTGTAACGATTTATTAACCTGGTCTTCTCAAAAAAAAAAAAAAAAAAAAAAAAAAAAAAAAA

FIGURE 1E

| 1 | AAA TGA AAA GGT TGT GCA GCT GAA TTC ATC CTT TTC TCT GAG | 42 |
|---|---|---|
|   | Asn Glu Lys Val Val Gln Leu Asn Ser Ser Phe Ser Leu Arg |   |
| 43 | ATG CTT TGG GGA GAG TGA AGT GAG CTG GCA GTA CCC ATG TCA | 84 |
|   | Cys Phe Gly Glu Ser Glu Val Ser Trp Gln Tyr Pro Met Ser |   |
| 85 | TGA AGA AGA GAG CTC CGA TGT GGA AAT CAG AAA TGA AGA AAA | 126 |
|   | Glu Glu Glu Ser Ser Asp Val Glu Ile Arg Asn Glu Glu Asn |   |
| 127 | CAA CAG CGG CCT TTC TGT GAC GGT CTT GGA AGT GAG CAG TGC | 168 |
|   | Asn Ser Gly Leu Ser Val Thr Val Leu Glu Val Ser Ser Ala |   |
| 169 | CTC GGC GGC CCA CAC AGG GTT GTA CAC TTG CTA TTA CAA CCA | 210 |
|   | Tyr Thr Cys Tyr Tyr Asn His Thr Gln Thr Glu Glu Asn Glu |   |
| 211 | CAC TCA GAC AGA AGA GAA TGA GCT TGA AGG CAG GCA CAT TTA | 252 |
|   | Leu Glu Ser Ala Ala His Thr Gly Leu Gly Arg His Ile Tyr |   |
| 253 | CAT CTA TGT GCC AGA CCC AGA TGT AGC CTT TGT ACC TCT AGG | 294 |
|   | Ile Tyr Val Pro Asp Pro Asp Val Ala Phe Val Pro Leu Gly |   |
| 295 | AAT GAC GGA TTA TTT AGT CAT CGT GGA GGA TGA TGA TTC TGC | 336 |
|   | Met Thr Asp Tyr Leu Val Ile Val Glu Asp Asp Asp Ser Ala |   |
| 337 | ·CAT TAT ACC TTG TCG CAC AAC TGA TCC CGA GAC TCC TGT AAC | 378 |
|   | Ile Ile Pro Cys Arg Thr Thr Asp Pro Glu Thr Pro Val Thr |   |
| 379 | CTT ACA CAA CAG TGA GGG GGT GGT ACC TGC CTC CTA CGA CAG | 420 |
|   | Leu His Asn Ser Glu Gly Val Val Pro Ala Ser Tyr Asp Ser |   |
| 421 | CAG ACA GGG CTT TAA TGG GAC CTT CAC TGT AGG GCC CTA TAT | 462 |
|   | Arg Gln Gly Phe Asn Gly Thr Phe Thr Val Gly Pro Tyr Ile |   |
| 463 | CTG TGA GGC CAC CGT CAA AGG AAA GAA GTT CCA GAC CAT CCC | 504 |
|   | Cys Glu Ala Thr Val Lys Gly Lys Lys Phe Gln Thr Ile Pro |   |
| 505 | ATT TAA TGT TTA TGC TTT AAA AGC AAC ATC AGA GCT GGA TCT | 546 |
|   | Phe Asn Val Tyr Ala Leu Lys Ala Thr Ser Glu Leu Asp Leu |   |
| 547 | AGA AAT GGA AGC TCT TAA AAC CGT GTA TAA GTC AGG GGA AAC | 588 |
|   | Glu Met Glu Ala Leu Lys Thr Val Tyr Lys Ser Gly Glu Thr |   |
| 589 | GAT TGT GGT CAC CTG TGC TGT TTT TAA CAA TGA GGT GGT TGA | 630 |
|   | Ile Val Val Thr Cys Ala Val Phe Asn Asn Glu Val Val Asp |   |
| 631 | CCT TCA ATG GAC TTA CCC TGG AGA AGT GAA AGG CAA GGC ATT | 672 |
|   | Leu Gln Trp Thr Tyr Pro Gly Glu Val Lys Gly Lys Gly Ile |   |

FIGURE 2A

673  CAC AAT GCT GGA AGA AAT CAA AGT CCC ATC CAT CAA ATT GGT  714
     Thr Met Leu Glu Glu Ile Lys Val Pro Ser Ile Lys Leu Val

715  GTA CAC TTT GAC GGT CCC CGA GGC CAC GGT GAA AGA CAG TGG  756
     Tyr Thr Leu Thr Val Pro Glu Ala Thr Val Lys Asp Ser Gly

757  AGA TTA CGA ATG TGC TGC CCG CCA GGC TAC CAG GGA GGT CAA  798
     Asp Tyr Glu Cys Ala Ala Arg Gln Ala Thr Arg Glu Val Lys

799  AGA AAT GAA GAA AGT CAC TAT TTC TGT CCA TGA GAA AGG TTT  840
     Glu Met Lys Lys Val Thr Ile Ser Val His Glu Lys Gly Phe

841  CAT TGA AAT CAA ACC CAC CTT CAG CCA GTT GGA AGC TGT CAA  882
     Ile Glu Ile Lys Pro Thr Phe Ser Gln Leu Glu Ala Val Asn

883  CCT GCA TGA AGT CAA ACA TTT GTT GTA GAG GTG CGG GCT A    924
     Leu His Glu Val Lys His Phe Val Val Glu Val Arg Ala Tyr

925  CCC ACC TCC CAG GAT ATC CTG GCT GAA AAA CAA TCT GAC TCT  966
     Pro Pro Pro Arg Ile Ser Trp Leu Lys Asn Asn Leu Thr Leu

967  GAT TGA AAA TCT CAC TGA GAT CAC CAC TGA TGT GGA AAA GAT  1008
     Ile Glu Asn Leu Thr Glu Ile Thr Thr Asp Val Glu Lys Ile

1009 ·TCA GGA AAT AAG GTA TCG AAG CAA ATT AAA GCT GAT CCG TGC  1050
     Gln Glu Ile Arg Tyr Arg Ser Lys Leu Lys Leu Ile Arg Ala

1051 TAA CCA AGA AGA CAG TGG CCA TTA TAC TAT TGT AGC TCA AAA  1092
     Asn Gln Glu Asp Ser Gly His Tyr Thr Ile Val Ala Gln Asn

1093 TGA AGA TGC TGT GAA GAG CTA TAC TTT TGA ACT GTT AAC TCA  1134
     Glu Asp Ala Val Lys Ser Tyr Thr Phe Glu Leu Leu Thr Gln

1135 AGT TCC TTC ATC CAT TCT GGA CTT GGT CGA TGA TCA CCA TGG  1176
     Val Pro Ser Ser Ile Leu Asp Leu Val Asp Asp His His Gly

1177 CTC AAC TGG GGG ACA GAC GGT GAG GTG CAC AGC TGA AGG CAC  1218
     Ser Thr Gly Gly Gln Thr Val Arg Cys Thr Ala Glu Gly Thr

1219 GCC GCT TCC TGA TAT TGA GTG GAT GAT ATG CAA AGA TAT TAA  1260
     Pro Leu Pro Asp Ile Glu Trp Met Ile  Cys Lys Asp Ile Lys

1261 GAA ATG TAA TAA TGA AAC TTC CTG GAC TAT TTT GGC AAC AA   1302
     Lys Cys Asn Asn Glu Thr Ser Trp Thr Ile Leu Ala Asn Asn

1303 TGT CTC AAA CAT CAT CAC GGA GAT CCA CTC CCG AGA CAG GAG  1344
     Val Ser Asn Ile Ile Thr Glu Ile His Ser Arg Asp Arg Ser

FIGURE 2B

```
1345 TAC CGT GGA GGG CCG TGT GAC TTT CGC CAA AGT GGA GGA GAC    1386
     Thr Val Glu Gly Arg Val Thr Phe Ala Lys Val Glu Glu Thr

1387 CAT CGC CGT GCG ATG CCT GGC TAA GAA TCT CCT TGG AGC TGA    1428
     Ile Ala Val Arg Cys Leu Ala Lys Asn Leu Leu Gly Ala Glu

1429 GAA CCG AGA GCT GAA GCT GGT GGC TCC CAC CCT GCG TTC TGA    1470
     Asn Arg Glu Leu Lys Leu Val Ala Pro Thr Leu Arg Ser Glu

1471 ACT CAC GGT GGC TGC TGC AGT CCT GGT GCT GTT GGT GAT TGT    1512
     Leu Thr Val Ala Ala Ala Val Leu Val Leu Leu Val Ile Val

1513 GAT CAT CTC ACT TAT TGT CCT GGT TGT CAT TTG GAA ACA GAA    1554
     Ile Ile Ser Leu Ile Val Leu Val Val Ile Trp Lys Gln Lys

1555 ACC GAG GTA TGA AAT CGC TGA GGG TCA TGA ATC AAT CAG        1596
     Pro Arg Tyr Glu Ile Arg Trp Arg Val Ile Glu Ser Ile Ser

1597 CCC GGA TGG ACA TGA ATA TAT TTA TGT GGA CCC GAT GCA GCT    1638
     Pro Asp Gly His Glu Tyr Ile Tyr Val Asp Pro Met Gln Leu

1639 GCC TTA TGA CTC AAG ATG GGA GTT CCA AGA TGG ACT AGT        1680
     Pro Tyr Asp Ser Arg Trp Glu Phe Pro Arg Asp Gly Leu Val

1681 GCT TGG TCG GGT CTT GGG GTC TGG AGC GTT TGG AAG GTG GT     1722
     Leu Gly Arg Val Leu Gly Ser Gly Ala Phe Gly Lys Val Val

1723 TGA AGG AAC AGC CTA TGG ATT AAG CCG GTC CCA ACC TGT CAT    1764
     Glu Gly Thr Ala Tyr Gly Leu Ser Arg Ser Gln Pro Val Met

1765 GAA AGT TGC AGT GAA CAT GCT AAA ACC ACG GCA GAT CAG        1806
     Lys Val Ala Val Asn Met Leu Lys Pro Thr Ala Arg Ser Ser

1807 TGA AAA ACA AGC TCT CAT GTC TGA ACT GAA GAT AAT GAC TCA    1848
     Glu Lys Gln Ala Leu Met Ser Glu Leu Lys Ile Met Thr His

1849 CCT GGG GCC ACA TTT GAA CAT TGT AAA CTT GCT GGG AGC CTG    1890
     Leu Gly Pro His Leu Asn Ile Val Asn Leu Leu Gly Ala Cys

1891 CAC CAA GTC AGG CCC CAT TTA CAT CAT CAC AGA GTA TTG CTT    1932
     Thr Lys Ser Gly Pro Ile Tyr Ile Ile Thr Glu Tyr Cys Phe

1933 CTA TGG AGA TTT GGT CAA CTA TTT GCA TAA GAA TAG GGA TAG    1974
     Arg Asp Ser Phe Leu Ser His His Pro Glu Lys Pro Lys Lys

1975 CTT CCT GAG CCA CCA CCC AGA GAA GCC AAA GAA AGA GCT GGA    2016
     Glu Leu Tyr Gly Asp Leu Val Asn Tyr Leu His Lys Asn Asp
```

FIGURE 2C

```
2017  TAT CTT TGG ATT GAA CCC TGC TGA TGA AAG CAC ACG GAG CTA    2058
      Ile Phe Gly Leu Asn Pro Ala Asp Glu Ser Thr Arg Ser Tyr

2059  TGT TAT TTT ATC TTT TGA AAA CAA TGG TGA CTA CAT GGA CAT    2100
      Val Ile Leu Ser Phe Glu Asn Asn Gly Asp Tyr Met Asp Met

2101  GAA GCA GGC TGA TAC TAC ACA GTA TGT CCC CAT GCT AGA AAG    2142
      Lys Gln Ala Asp Thr Thr Gln Tyr Val Pro Met Leu Glu Arg

2143  GAA AGA GGT TTC TAA ATA TTC GAC GTC CAG AGA TCA CTC TA     2184
      Lys Glu Val Ser Lys Tyr Ser Asp Val Gln Arg Ser Leu Tyr

2185  TGA TCG TCC AGC CTC ATA TAA GAA GAA ATC TAT GTT AGA CTC    2226
      Asp Arg Pro Ala Ser Tyr Lys Lys Lys Ser Met Leu Asp Ser

2227  AGA AGT CAA AAA CCT CCT TTC AGA TGA TAA CTC AGA AGG CCT    2268
      Glu Val Lys Asn Leu Leu Ser Asp Asp Asn Ser Glu Gly Leu

2269  TAC TTT ATT GGA TTT GTT GAG CTT CAC CTA TCA AGT TGC CCG    2310
      Thr Leu Leu Asp Leu Leu Ser Phe Thr Tyr Gln Val Ala Arg

2311  AGG AAT GGA GTT TTT GGC TTC AAA AAA TTG TGT CCA CCG TGA    2352
      Gly Met Glu Phe Leu Ala Ser Lys Asn Cys Val His Arg Asp

2353 •TCT GGC TGC TCG CAA CGT CCT CCT GGC ACA AGG AAA AAT TGT    2394
      Leu Ala Ala Arg Asn Val Leu Leu Ala Gln Gly Lys Ile Val

2395  GAA GAT CTG TGA CTT TGG CCT GGC CAG AGA CAT CAT GCA TGA    2436
      Lys Ile Cys Asp Phe Gly Leu Ala Arg Asp Ile Met His Asp

2437  TTC GTT CTA TGT GTC GAA AGG CAG TAC CTT TCT GCC CGT GAA    2478
      Ser Phe Tyr Val Ser Lys Gly Ser Thr Phe Leu Pro Val Lys

2479  GTG GAT GGC TCC TGA GAG CAT CTT TGA CAA CCT CTA CAC CAC    2520
      Trp Met Ala Pro Glu Ser Ile Phe Asp Asn Leu Tyr Thr Thr

2521  ACT GAG TGA TGT CTG GTC TTA TGG CAT TCT GCT CTG GGA GAT    2562
      Leu Ser Asp Val Trp Ser Tyr Gly Ile Leu Leu Trp Glu Ile

2563  CTT TTC CCT TGG TGG CAC CCC TTA CCC CGG CAT GAT GGT GGA    2604
      Phe Ser Leu Gly Gly Thr Pro Tyr Pro Gly Met Met Val Asp

2605  TTC TAC TTT CTA CAA TAA GAT CAA GAG TGG GTA CCG GAT GGC    2646
      Ser Thr Phe Tyr Asn Lys Ile Lys Ser Gly Tyr Arg Met Ala

2647  CAA GCC TGA CCA CGC TAC CAG TGA AGT CTA CGA GAT CAT GGT    2688
      Lys Pro Asp His Ala Thr Ser Glu Val Tyr Glu Ile Met Val
```

FIGURE 2D

```
2689 GAA ATG CTG GAA CAG TGA GCC GGA GAA GAG ACC CTC CTT TTA    2730
     Lys Cys Trp Asn Ser Glu Pro Glu Lys Arg Pro Ser Phe Tyr

2731 CCA CCT GAG TGA GAT TGT GGA GAA TCT GCT GCC TGG ACA ATA    2772
     His Leu Ser Glu Ile Val Glu Asn Leu Leu Pro Gly Gln Tyr
2773 TAA AAA GAG TTA TGA AAA AAT TCA CCT GGA CTT CCT GAA GAG    2814
     Lys Lys Ser Tyr Glu Lys Ile His Leu Asp Phe Leu Lys Ser

2815 TGA CCA TCC TGC TGT GGC ACG CAT GCG TGT GGA CTC AGA CAA    2856
     Asp His Pro Ala Val Ala Arg Met Arg Val Asp Ser Asp Asn

2857 TGC ATA CAT TGG TGT CAC CTA CAA AAA CGA GGA AGA CAA GCT    2898
     Ala Tyr Ile Gly Val Thr Tyr Lys Asn Glu Glu Asp Lys Leu

2899 GAA GGA CTG GGA GGG TGG TCT GGA TGA GCA GAG ACT GAG CGC    2940
     Lys Asp Trp Glu Gly Gly Leu Asp Glu Gln Arg Leu Ser Ala

2941 TGA CAG TGG CTA CAT CAT TCC TCT GCC TGA CAT TGA CCC TGT    2982
     Asp Ser Gly Tyr Ile Ile Pro Leu Pro Asp Ile Asp Pro Val

2983 CCC TGA GGA GGA GGA CCT GGG CAA GAG GAA CAG ACA CAG CTC    3024
     Pro Glu Glu Glu Asp Leu Gly Lys Arg Asn Arg His Ser Ser

3025 GCA GAC CTC TGA AGA GAG TGC ATT GAA ACG GGT TCA GCA G      3066
     Gln Thr Ser Glu Glu Ser Ala Ile Glu Thr Gly Ser Ser Ser

3067 TTC ACC TTT CAT CAA GAG AGA GGA CGA GAC CAT TGA AGA CAT    3108
     Ser Thr Phe Ile Lys Arg Glu Asp Glu Thr Ile Glu Asp Ile

3109 CGA CAT GAT GGA CGA CAT CGG CAT AGA CTC TTC AGA CCT GGT    3150
     Asp Met Met Asp Asp Ile Gly Ile Asp Ser Ser Asp Leu Val

3151 GGA AGA CAG CTT CCT GTA ACT GGC GGA TTC GAG GGT CCT TC     3192
     Glu Asp Ser Phe Leu  *  Leu Ala Asp Ser Arg Val Pro Ser

3193 CAC TTC T        3199
     Thr Ser
```

FIGURE 2E

HUMAN PLATELET-DERIVED GROWTH FACTOR RECEPTOR, TYPE A

CROSS REFERENCE TO RELATED APPLICATION

The present application is a continuation of application Ser. No. 08/031,082 filed Mar. 15, 1993, now abandoned, which is a continuation of application No. 07/771,829 filed Oct. 7, 1991, now abandoned, which is a continuation of application Ser. No. 07/309,322 filed Feb. 10, 1989, now abandoned, which is a Continuation-In-Part of U.S. application Ser. No. 07/151,414 filed Feb. 2, 1988, now abandoned, and entitled Human Platelet-Derived Growth Factor Receptor (Williams and Escobedo), which application is incorporated herein by reference.

This invention was made with Government support under Grant No. RO 1 HL 32898 awarded by the National Institutes of Health. The Government has certain rights in this invention.

INTRODUCTION

1. Technical Field

The present invention relates to growth factors and their receptors and, in particular, to human platelet-derived growth factor receptor.

2. Background of the Invention

Platelet-derived growth factor (PDGF) is a major mitogen for cells of mesenchymal origin. The protein is a 32 kDa protein heterodimer composed of two polypeptide chains, A and B, linked by disulfide bonds. In addition to the PDGF AB heterodimer, two homodimeric forms of PDGF, denoted AA and BB, have been identified.

Until recently, whether the AA isoform bound to a receptor was not known. Now, a single receptor has been identified which has been shown to bind all three isoforms of hPDGF. However, the reported affinities of hPDGF receptors of different cell types for different isoforms of hPDGF has lead to speculation that there are more than one type of hPDGF receptor.

The first event in PDGF-mediated mitogenesis is the binding of PDGF to its receptor at the cell membrane. This interaction triggers a diverse group of early cellular responses including activation of receptor tyrosine kinase, increased phosphatidylinositol turnover, enhanced expression of a group of genes, activation of phospholipase A2, changes in cell shape, increase in cellular calcium concentration, changes in intracellular pH, and internalization and degradation of bound PDGF. These changes are followed by an increase in the rate of proliferation of the target cells.

While the ability of a polypeptide to stimulate growth of a particular cell type in vitro does not prove that it serves the same function in vivo, the role of many growth factors on cells is being studied to attempt to determine the role that the factors play in the whole organism. In vitro, platelet-derived growth factor is a major polypeptide mitogen in serum for cells of mesenchymal origin such as fibroblasts, smooth muscle cells and glial cells. In vivo, PDGF circulates stored in the a granules of blood platelets and does not circulate freely in blood. During blood clotting and platelet adhesion, the granules are released, often at sites of injured blood vessels, implicating PDGF in the repair of blood vessels. PDGF also stimulates migration of arterial smooth muscle cells from the medial to the intimal layer of the artery where they then proliferate as an early response to injury.

PDGF is being studied to determine how cell proliferation is controlled in the body. The growth factor has been implicated in wound healing, in atherosclerosis, and in stimulating genes associated with cancerous transformation of cells, particularly c-myc and c-fos. Therefore, PDGF agonists may be useful in promoting wound healing. PDGF antagonists may be useful in preventing atherosclerosis, in retarding blood vessel narrowing that occurs after cardiovascular intervention and in controlling cancerous proliferation.

Relevant Literature

The mouse PDGF receptor has been identified, purified (Daniel et al., *Proc. Natl. Acad. Sci USA* (1985) 82:2684–2687), and sequenced (Yarden et al., *Nature* (1986) 323:226–232). A cDNA sequence encoding a human PDGF receptor was identified, sequenced and used to transfect cells lacking the receptor (Escobedo et al., *Science* (1988) 240:1532–1538; Claesson-Welsh et al., *Mol. Cell. Biol.* (1988) 8:3476–3486). Studies using the transfected cells gave differing results, demonstrating that the receptor binds specifically to all three isoforms of hPDGF, preferentially binding the BB homodimer (Escobedo et al., supra.) and that the receptor binds the BB and AB isoforms but not the AA isoform, at least at the concentration tested (Claesson-Welsh et al., supra.). Binding sites on different cell types were reported to have different affinities for different PDGF isoforms (Kazlauskas et al., *EMBO J.* (1988) 7:3727–3735). Two classes of PDGF receptor were reported to recognize different isoforms of PDGF (Hart et al., *Science* (1988) 240:1529–1531).

SUMMARY OF THE INVENTION

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

BRIEF DESCRIPTION OF THE FIGURES

FIG. 1 shows the nucleotide sequence of a cDNA encoding B-hPDGF-R together with the deduced amino acid sequence of the receptor precursor.

FIG. 2 shows the nucleotide sequence of a cDNA encoding A-hPDGF-R together with the deduced amino acid sequence of the receptor.

DESCRIPTION OF SPECIFIC EMBODIMENTS

Methods for producing human platelet-derived growth factor (hPDGF-R) and nucleic and constructs for such production are provided as well as cells comprising the hPDGF-R where the composition and cells may find use in diagnosis, evaluation of drugs affecting the transduction of the hPDGF-R signal and in the treatment of diseases associated with hPDGF-R. The construct can be used to transfect cells, providing a membrane-bound receptor that is functionally equivalent to the wild-type receptor, and conferring a PDGF-sensitive mitogenic response on cells lacking the receptor. The transfected cells can be used as a model for studying the PDGF-induced response of cells, determining the regions involved in transducing the signal in response to PDGF binding and evaluating drugs for their physiologic activity. The encoded receptor or its binding region also find use in evaluating PDGF agonists. Other utilities for the DNA sequence include use of fragments of the sequence as probes to detect deletions in the region of chromosome 5 where a number of growth-control related genes are clustered, to detect deletions in chromosome 4 near the c-kit oncogene or to detect other genes encoding tyrosine kinase or homologous proteins.

The hPDGF receptor that binds the BB homodimer with high affinity has been variously referred as the B receptor, the β receptor and, as used herein, the type B receptor (B-hPDGF-R). The hPDGF receptor that preferentially binds the AA homodimer is referred to as the A receptor, the α receptor and, as used herein, the type A receptor (A-hPDGF-R).

Figure 1A:
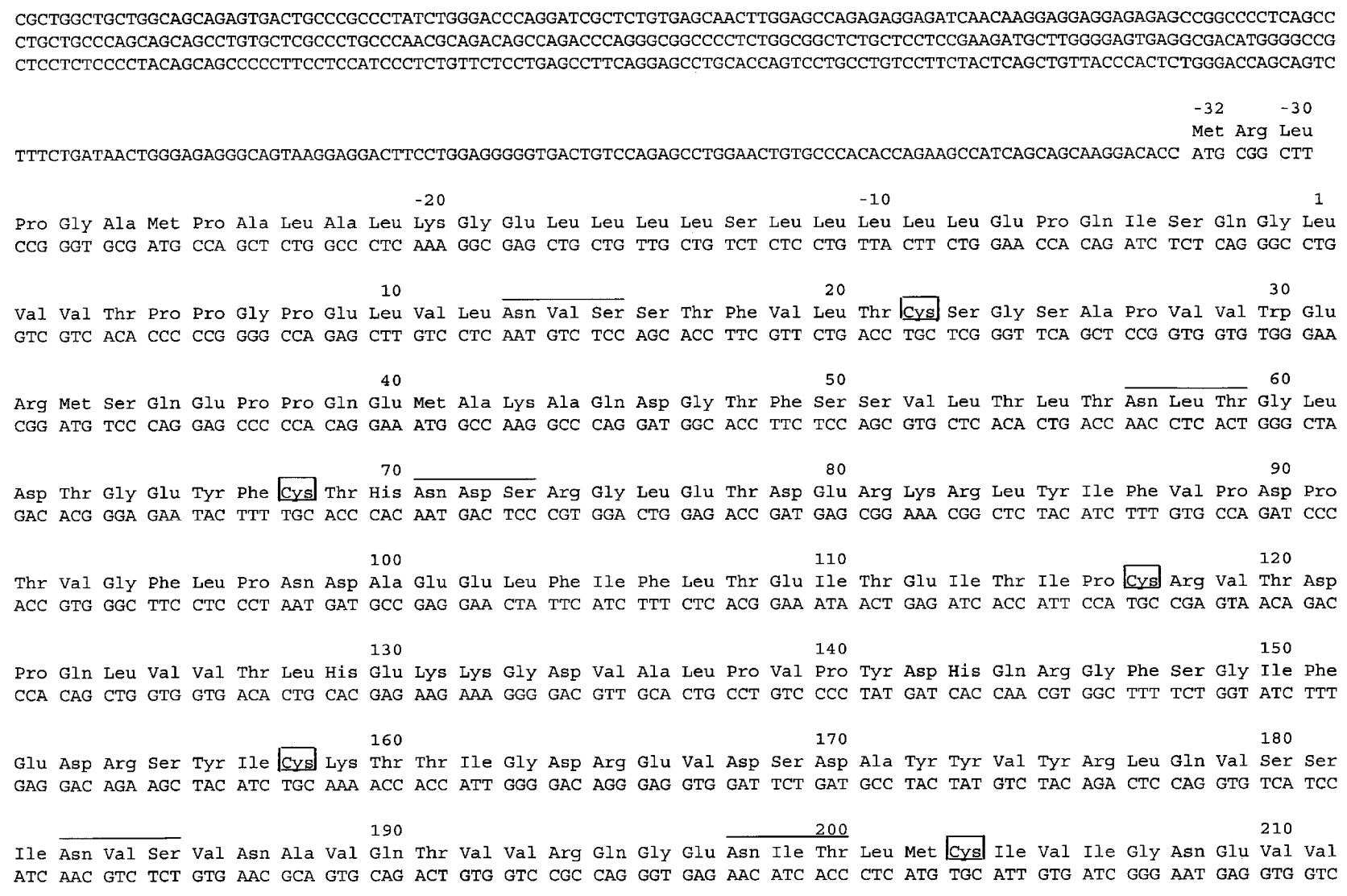

The nucleotide sequence of a cDNA sequence encoding B-hPDGF-R is set forth in FIG. 1 together with the deduced amino acid sequence of the receptor precursor. The sequence beginning at the amino acid numbered 1 corresponds to the amino terminus of human PDGF-R. The first 32 amino acids (designated −32 to −1) encode the signal peptide sequence. The dark bar underlines the transmembrane sequence (amino acid residues 500 to 524). Potential N-glycosylation sites are indicated by a line. The polyadenylation site in the 3' end of the cDNA has been underlined.

The nucleotide sequence of a cDNA sequence encoding A-hPDGF-R is set forth in FIG. 2 together with the deduced amino acid sequence of the receptor. The sequence of the 3' untranslated region and the signal sequence-encoding region are not shown. The reading frame for the amino acid sequence begins at nucleotide 2. The "*" at nucleotides 3167–3169 (TAA) indicates a stop codon for chain termination of the receptor protein sequence. The coding sequence for the extracellular domain is from nucleotide 1 through 1471. The transmembrane region is from 1472 through 1546. The intracellular region is from 1547–3166. The tyrosine kinase region is encoded by residues 1669–1982 and 2279 to about 2700.

As seen in FIGS. 1 and 2, the intracellular, tyrosine kinase domain of the type A and type B receptors have about 80% identical residues. The extracellular domain of the type A and B receptors have about 34–35% identical residues, an additional 14% of the remaining residues being conservative substitutions. The transmembrane regions of the hPDGF receptors have about 48% identical residues. Of the 52% of residues that differ, 70% are conservative substitutions. As seen in the tables, both receptor sequences have a 107 amino acid insertion interrupting the tyrosine kinase region (encoded by residues 1983–2278 of type A).

The DNA compositions of this invention may be derived from genomic DNA or cDNA, prepared by synthesis or combinations thereof. The DNA compositions may include the complete coding region encoding hPDGF-R or fragments thereof of interest, usually comprising at least 8 codons (24 bp), more usually at least 12 codons, where one or more introns may be present. While for the most part the wild-type sequence will be employed, in some situations one or more mutations may be introduced, such as deletions, substitutions or insertions resulting in changes in the amino acid sequence or providing silent mutations. The genomic sequence will usually not exceed 50 kbp, more usually not exceed about 10 kbp, preferably not greater than 6 kbp.

A DNA fragment encoding hPDGF-R finds use to isolate DNA encoding PDGF receptors of other species which share substantial homologies with hPDGF-R. Fragments from the intracellular tyrosine kinase region can be used to isolate other tyrosine kinases. Portions of the DNA fragment having at least about 10 nucleotides, usually at least about 20 nucleotides, and fewer than about 6 knt (kilonucleotides), usually fewer than about 0.5 knt, from a DNA sequence encoding hPDGF-R find use as probes. The probes can be used to determine whether mRNA encoding hPDGF-R is present in a cell.

Additionally, the type B human PDGF receptor gene is located at a site on chromosome 5 where a number of growth control related genes are clustered. At least one genetic disease, 5q minus syndrome, has been shown to involve a deletion in this region. The type A receptor gene is located on chromosome 4 near the c-kit oncogene. Fragments of the hPDGF-R gene sequence may be used as a marker to probe the structure of these important regions of the genome and to diagnose genetic diseases associated with those areas of the genome.

The DNA fragment or portions thereof can also be used to prepare an expression construct for hPDGF-R. The construct comprises one or more DNA sequences encoding hPDGF-R under the transcriptional control of the native or other than the native promoter. When more than one sequence encoding hPDGF-R is present in the construct, the sequences may encode the same or different isoforms of the receptor, usually different. Usually the promoter will be a eukaryotic promoter for expression in a mammalian cell, where the mammalian cell may or may not lack PDGF receptors. In cases where one wishes to expand the DNA sequence or produce the receptor protein or fragments thereof in a prokaryotic host, the promoter may also be a prokaryotic promoter. Usually a strong promoter will be employed to provide for high level transcription and expression.

The expression construct may be part of a vector capable of stable extrachromosomal maintenance in an appropriate cellular host or may be integrated into host genomes. The expression cassette may be bordered by sequences which allow for insertion into a host, such as transposon sequences, lysogenic viral sequences, or the like. Normally, markers are provided with the expression cassette which allow for selection of host cells containing the expression cassette. The marker may be on the same or a different DNA molecule, desirably the same DNA molecule.

In mammalian cells, the receptor gene itself may provide a convenient marker. However, in prokaryotic cells, markers such as resistance to a cytotoxic agent, complementation of an auxotrophic host to prototrophy, production of a detectable product, etc. will be more convenient.

The expression construct can be joined to a replication system recognized by the intended host cell. Various replication systems include viral replication systems such as retroviruses, simian virus, bovine papilloma virus, or the like In addition, the construct may be joined to an amplifiable gene, e.g., DHFR gene, so that multiple copies of the hPDGF-R gene may be made.

Introduction of the construct into the host will vary depending upon the particular construction. Introduction can be achieved by any convenient means, including fusion, conjugation, transfection, transduction, electroporation, injection, or the like, as amply described in the scientific literature. Introduction of constructs encoding different isoforms of the receptor into a single host cell is also contemplated. The host cells will normally be immortalized cells, that is cells that can be continuously passaged in culture. For the most part, these cells may be any convenient mammalian cell line which is able to express hPDGF-R and where desirable, process the polypeptide so as to provide a mature polypeptide. By processing is intended glycosylation, ubiquitination, disulfide bond formation, or the like. Usually the host will be able to recognize the signal sequence for inserting hPDGF-R into the membrane of the cell. If secretion is desired, the transmembrane locator sequence may be deleted or mutated to prevent membrane insertion of the protein.

A wide variety of hosts may be employed for expression of the peptides, both prokaryotic and eukaryotic. Useful hosts include bacteria, such as E. coli, yeast, filamentous fungus, immortalized mammalian cells, such as various mouse lines, monkey lines, Chinese hamster ovary lines, human lines, or the like. For the most part, the mammalian cells will be immortalized cell lines. In some cases, the cells may be isolated from a neoplastic host, or wild-type cells may be transformed with oncogenes, tumor causing viruses, or the like.

Under may circumstances, it will be desirable to transfect mammalian cells which lack a PDGF receptor where the signal sequence directs the peptide into the cell membrane. Lymphocytes and cardiac myocytes are primary cells which lack a receptor. Also, Chinese hamster ovary cells (CHO), epithelial cells lines and a number of human tumor cell lines lack PDGF receptors.

Transfected cells find use as a model for studying cellular responses to PDGF. For controlled investigation, mammalian cells which lack a PDGF receptor can be transfected with an expression construct comprising a DNA sequence encoding hPDGF-R. Cells are produced that encode a receptor that is functionally equivalent to the wild-type receptor and confer a PDGF-sensitive mitogenic response on the cell. In this way, the binding properties of the naturally-occurring PDGF may be analyzed, fragments tested as well as synthetic compounds both proteinaceous and non-proteinaceous. As demonstrated in the Experimental section, transfected cells were used to determine that the AA form of PDGF activates the type B receptor tyrosine kinase. The presence of the type A and type B receptors in a single cell facilitates the study of receptor binding properties.

In addition to studying PDGF-mediated mitogenesis, the transfected cells can be used to evaluate a drug's ability to function as a PDGF agonist or antagonist. In particular, transfected cells can be contacted with the test drug, and the amount of receptor tyrosine kinase activation or the rate of DNA synthesis can be determined in comparison to control cells in the presence or absence of PDGF, or analogs thereof of known activity.

The hPDGF-R protein expressed by transfected cells also finds use. If the peptide is secreted, the peptide may be isolated from the supernatant in which the expression host is grown. If not secreted, the peptide may be isolated from a lysate of the expression host. The peptide may then be isolated by convenient techniques employing HPLC, electrophoresis, gradient centrifugation, affinity chromatography, particularly using PDGF, etc., to provide a substantially pure product, particularly free of cell component contaminants.

The receptor protein or amino acids beginning at about 33 through about 500 of the amino terminal sequence of the receptor which form the external domain, binding portion of the receptor protein find use to affinity purify PDGF. The external domain can also be used affixed to a solid substrate or free in solution to determine drugs useful as PDGF agonists and antagonists.

The protein or the intracellular portion of the protein, beginning at about amino acid 525 through the carboxy terminal amino acid of hPDGF-R, also find use as an enzyme having tyrosine kinase activity. Additionally, amino acids 1 through 32 of the amino terminal sequence of the type B receptor comprise a signal sequence which directs the structural protein through the membrane of a transfected cell. The signal sequence can be used with hPDGF-R, but also finds use with other proteins.

Peptides or portions thereof may also be used for producing antibodies, either polyclonal or monoclonal. Antibodies are produced by immunizing an appropriate vertebrate host, e.g., mouse, with the peptide itself, or in conjunction with a conventional adjuvant. Usually two or more immunizations will be involved, and the blood or spleen will be harvested a few days after the last injection.

For polyclonal antisera, the immunoglobulins may be precipitated, isolated and purified, including affinity purification. For monoclonal antibodies, the splenocytes normally will be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570 and 4,618,577.

The following examples are offered by way of illustration and not by way of limitation.

EXPERIMENTAL

Screening of Human Kidney λGT11 cDNA Library and Human Placenta λGT10 cDNA Library A full-length DNA sequence encoding the mouse PDGF receptor (mPDGF-R) protein was used as a probe to screen 250,000 plaques of a human kidney cDNA library. Nick translation was used to prepare a probe with specific activity of $12 \times 10^8$ cpm per µg. The filters were incubated with the probe ($10^5$ cpm per ml) in hybridization buffer containing 30% formamide, 1× Denhardt's solution, 5× SC, 0.02M sodium phosphate pH 6.5 and 500 µg per ml of salmon sperm DNA. After 14 hr. of hybridization at 40° C, the filters were washed four times at 55° C. with 0.2× SSC and 0.1% SDS and two additional times at 65° C. with 0.2× SSC. The filters were then air dried and exposed for 16 hrs.

Ten positive clones were obtained which were rescreened with the full-length mPDGF-R probe. Individual clones were isolated and analyzed by restriction analysis using EcoRI endonuclease. The clone containing the largest insert (2.3 kb), designated clone HK-6, was further characterized and sequenced using dideoxy terminators. Clone HK-6 contained the receptor sequence from nucleotide 3554 to nucleotide 5691 plus nine bases from the poly A tail.

A nick-translated probe, prepared from the 2.3 kb HK-6 DNA, was used to screen 250,000 plaques of a human placenta cDNA library. This screening was performed at high hybridization stringency (50% formamide in the hybridization buffer described above). The filters were incubated with $5 \times 10^5$ cpm per ml of probe for 14–16 hrs. at 42° C. The filters were than washed at 65° C. in 0.1% SSC and 0.1% SDS four times.

After secondary screening with the HK-6 probe, seven clones were selected and analyzed by restriction digestion with EcoRI endonuclease. A clone (HP-7) that contained a 4.5 kb insert was selected and characterized. The sequence of that clone is described in FIG. 1 and encodes the type B human PDGF receptor (B-hPDGF-R).

Construction of Expression Vector

The 4.5 kb DNA fragment containing the complete coding sequence for the type B human PDGF receptor was isolated from the HP-7 clone by EcoRI digestion. The gel purified fragment was cloned into the EcoRI site in the polylinker region of SV40 expression vector PSV7C. The pSV7d expression vector (provided by P. Luciw, University of California, Davis) was a pML derivative containing the SV40 early promoter region (SV40 nucleotides 5190–5270), a synthetic polylinker with restriction sites for EcoRI, SmaI, XbaI, and SalI followed by three translation terminator codons (TAA) and the SV40 polyadenylation signal (SV40 nucleotides 2556–2770) (Truett et al., *DNA* (1984) 4:333–349). The EcoRI fragment containing the cDNA sequence obtained from the HP-7 clone was inserted at the EcoRI site of the pSV7d. In the resulting expression vector, the B-hPDGF-receptor gene was under transcriptional control of the SV40 promoter.

To ensure the proper orientation of the PDGF receptor insert (4.5 kb) with respect to the SV40 promoter, the positive clones were digested with SmaI endonuclease which cuts at position 573 of the receptor sequence and in the polylinker region of the expression vector.

Clones containing the receptor in the proper transcriptional orientation released a 4.0 kb insert in addition to the 3.2 kb fragment containing the expression vector plus 573 base pairs of the 5' end of the receptor. This plasmid, PSVRH5 was used to co-transfect cells with PSV2 neo plasmid that confers resistance to the antibiotic neomycin.

Cell Culture and Transfection of CHO Cells

CHO cell clone KI, obtained from the U.C.S.F. Tissue Culture Facility, were grown in Ham's F-12 media supplemented with 10% FCS (U.C.S.F. Tissue Culture Facility) and penicillin and streptomycin at 37° C. in 5% $CO_2$/95% air.

pSVRH5 plasmid DNA (10 μu) and pSV2 neo (1 μg) were used to co-transfect $1 \times 10^6$ CHO cells by the calcium precipitation technique (Van der Eb et al., *Methods Enzymology* (1980) 65:826–839), with the addition of 10 μg chloroquinone diphosphate (CDP) to prevent degradation of the transfected DNA (Luthman and Magnusson, *Nucl. Acid Res.* (1983) 11:1295–1308). After 12 hrs. of exposure to the DNA, the cells were trypsinized and replated at 1:5 dilution. Twenty-four hours later, the antibiotic G418 (GIBCO), an analog of neomycin, was added to the cultures at a concentration of 400 μg/ml.

After two weeks under selection, independent colonies were picked and transferred to 24-well plates. Confluent cultures were assayed for the presence of PDGF receptor by immunoblot using anti-receptor antibodies. Colonies that were positive by this assay were single-cell cloned by end-limiting dilution.

Stable transfected clones were tested for the expression of the type B PDGF receptor message measured by RNA protection assays (Zinn et al., *Cell* (1983) 34:865–879) and for the presence of PDGF-stimulated receptor protein detected by antiphosphotyrosine antibodies (Frackelton et al., *J. Biol. Chem.* (1984) 259:7909–7915).

Expression of B-hPDGF-R cDNA in CHO Cells

CHO cells transfected with plasmid DNA containing the human receptor cDNA under the transcriptional control of the SV40 early promoter (CHO-HR5) and CHO cells transfected with a similar plasmid containing the mouse receptor cDNA (CHO-R18) were solubilized as previously described (Escobedo et al., *J. Biol. Chem.* (1988) 263:1482–1487).

Extracts were analyzed by Western blot analysis using an antibody that specifically recognizes sequences in the receptor carboxy-terminal region as previously described in (Escobedo et al., supra; Keating et al., ibid. (1987) 262:7932–7937). The 195 kDa protein is the mature receptor and the 160 kDa protein is the receptor precursor.

The expression of the receptor protein in the transfectants was demonstrated by using antibodies that recognize an intracellular sequence in the receptor. The clone that had the highest level of human receptor expression was chosen for further study. This transfectant had receptors that were labeled with $^{125}$I-PDGF as shown by the competitive binding studies described below.

Competitive Binding of the Different Forms of PDGF to the Type B Receptor

The ability of the human recombinant AA and BB homodimers (Collins et al., *Nature* (1987) 328:621–624) to compete for the type B receptor sites and displace $^{125}$I-labeled PDGF was studied. Each homodimer was produced selectively by a yeast expression system (Brake et al., *Proc. Natl. Acad. Sci.* (*USA*) (1984) 81:4642–4646) and was purified from yeast media that is devoid of other mesenchymal cell growth factors, thus avoiding the artifact of contamination by factors that might be present in mammalian expression systems.

BALB/c 3T3 cells and CHO transfectants (CHO-HR5) were incubated with $^{125}$I-PDGF (Williams et al., ibid (1982) 79:5067–5070) in the presence of increasing concentrations of AA or BB. Binding was carried out at 37° C. for 45 min. in whole cell suspension. Unbound, radiolabeled PDGF was removed by centrifugation on a Ficoll gradient (Orchansky et al., *J. Immunol.* (1986) 136:169–173). Non-specific binding, determined by incubating CHO cells with $^{125}$I-PDGF, accounted for 25 percent of the bound radioactivity.

The binding study demonstrated that the transfected cells can be used as a model to study the interaction of hPDGF with its receptor. In particular, this study demonstrated that the transfected type B human receptor was functionally identical to the native mouse receptor as indicated by the following results. Both AA and BB forms of PDGF competed for the $^{125}$I-PDGF labeled sites in the human receptor transfectants. For the transfected type B human receptor as well as the native mouse receptor, the BB form was of higher affinity than the AA form. When expressed in yeast, the AA form of PDGF may be processed aberrantly, giving it a lower affinity than the BB form for both the transfected cells and mouse 3T3 cells. The consistency of the pattern of competition shows that the AA form interacts with the transfected type B human receptor in the same way as it does with the native mouse receptor and demonstrates that these receptors are functionally identical.

Activation of the PDGF Receptor Tyrosine Kinase

The ability of recombinant AA and BB homodimers and of human partially purified AB PDGF to activate the type B receptor tyrosine kinase was studied. The yeast-derived AA and BB homodimeric forms and the platelet-derived AB form stimulated autophosphorylation of the transfected human receptor.

BALB/c 3T3 cells and CHO cells transfected with the human PDGF receptor cDNA (CHO-HR5) were incubated with increasing amounts of the different forms of PDGF (AA, BB and AB). Following polyacrylamide-SDS electrophoresis, the phosphorylated receptor was identified by Western blot using an antiphosphotyrosine antibody (Wang, *Mol. Cell. Biol.* (1985) 5:3640–3643). The receptor protein co-migrated with the 200 kDa molecular weight marker. The concentration of each form that was effective in stimulating autophosphorylation of the transfected human receptor was identical to the concentration that gave a similar autophosphorylation to the native mouse 3T3 receptor or the transfected mouse receptor.

These results showed for the first time that the AA form of PDGF activates the receptor tyrosine kinase of the type B receptor. Prior to use of the transfected cells, there was no demonstration that the AA form had hPDGF activity or that a single receptor, the type B receptor, was capable of recognizing all three forms of PDGF. Further, the results demonstrate that the human cDNA encodes a type B receptor that is functionally equivalent to the wild-type receptor that is responsible for PDGF-stimulated tyrosine kinase activity in mouse 3T3 cells.

Thus, the transfected cells are useful models for studying PDGF-induced mitogenic responses.

Rate of DNA Synthesis in CHO Transfected Cells

BALB/c 3T3 cells and CHO cells transfected with the type B human PDGF receptor cDNA (CHO-HR5) were incubated with saturating concentrations of the three forms of PDGF. Untreated cells and cells treated with fetal calf serum (FCS) were used as negative and positive controls, respectively. The level of $^3$H-thymidine incorporation into DNA was determined by measuring the radioactivity of the acid-precipitable material as previously described (Escobedo, supra).

Transfection of CHO cells with either human type B or mouse PDGF receptor conferred a PDGF-sensitive mitogenic response. All forms of PDGF stimulated DNA synthesis in both the type B human receptor transfectant and the mouse cells bearing the native receptor.

These data showed that the A chain homodimer and the B chain homodimer, like the AB platelet-derived form, were mitogens that can act through the receptor encoded by the type B human cDNA sequence. The mitogenic action of these forms of PDGF on mouse 3T3 cells and CHO cells containing the transfected type B human receptor demonstrate that the responses were mediated by functionally identical receptors.

Isolation and Expression of the Type A PDGF Receptor

The type A receptor was isolated as described for the type B receptor, above, except that different probes were used and hybridization and screening were performed under low stringency conditions, as described below. In particular, a region in the type B receptor tyrosine kinase sequence having a high degree of homology to published tyrosine kinase amino acid sequences was identified and had the amino acid sequence, HRDLAARN. oligonucleotide probes encoding the tyrosine kinase consensus sequence were prepared having the following sequences:

GTT(G/C)CGXGCXGCCAGXTC(G/C)CGXTG, where G/C indicates either G or C was used and X indicates any of A, T, C or G was used. The human placenta λGT10 cDNA library was screened as described above but with low stringency conditions using a buffer with 6× SSC 0.1% SDS and 5× Denhardt's solution at 42° C. as follows. Filters were screened by washing at 52° C. in 2× SSC. A clone encoding the type A receptor was isolated and sequenced by the procedure described for the type B receptor gene.

The DNA sequence of the gene encoding the type A receptor (A-hPDGF-R) together with the deduced amino acid sequence are shown in FIG. 2, above.

The clone encoding A-hPDGF-R was digested, gel purified and inserted into the SV40 expression vector, pSV7C, as described for the type B receptor clone.

That vector is used to transfect CHO cells as described above for the type B receptor. With expression of the vector coding sequence, transfected CHO cells produce a functional receptor that binds all three hPDGF isoforms, preferentially binding the AA homodimer.

These studies were made possible by the availability of growth factor preparations devoid of contamination with other growth factors and by the use of a receptor expression system in which all of the measured PDGF responses could be attributed to this single transfected receptor cDNA.

All publications and patent applications herein are incorporated by reference to the same extent as if each individual publication or patent application was specifically and individually indicated to be incorporated by reference. The invention now being full described, it will be apparent to one of ordinary skill in the art that many changes and modifications can be made thereto without departing from the spirit or scope of the appended claims.

What is claimed is:

1. A DNA fragment comprising at least eight contiguous codons of the nucleotide sequence shown in FIG. 2.

2. A DNA fragment according to claim 1 comprising the nucleotide sequence shown in FIG. 2.

3. A DNA fragment encoding a type A human platelet-derived growth factor receptor.

4. An expression construct that expresses a type A human platelet-derived growth factor receptor polypeptide when introduced into a cell, said construct comprising in the 5'-3' direction of transcription: a SV40 early promoter and under the transcriptional regulation of said promoter, a DNA sequence encoding said type A human platelet-derived growth factor receptor polypeptide joined to DNA other than DNA naturally joined to said type A human platelet-derived growth factor receptor polypeptide-encoding DNA sequence.

5. A Chinese hamster ovary cell transfected by an expression construct according to claim 4.

6. A cell according to claim 5 wherein prior to said transfection said cell is hPDGF-R⁻.

7. An isolated DNA molecule encoding a human platelet-derived growth factor type A receptor, wherein said receptor comprises the amino acid sequence of FIG. 2 from asparagine, amino acid number 1, to leucine, amino acid number 1055.

8. Eukaryotic cells transfected with a DNA construct under the transcriptional control of a promoter, said construct comprising a DNA molecule encoding a human platelet-derived growth factor type A receptor, wherein said receptor comprises the amino acid sequence of FIG. 2 from asparagine, amino acid number 1, to leucine, amino acid number 1055.

9. The cells of claim 8 wherein said cells are cultured mammalian cells.

10. The cells of claim 8, wherein said cells are yeast cells.

* * * * *